(12) United States Patent
Sen et al.

(10) Patent No.: US 8,192,755 B2
(45) Date of Patent: Jun. 5, 2012

(54) PHARMACEUTICAL COMPOSITION FOR CONTROLLED RELEASE OF A BETA-LACTAM ANTIBIOTIC

(75) Inventors: Himadri Sen, Aurangabad (IN); Rajesh Suresh Kshirsagar, Aurangabad (IN); Shailesh Suresh Bhamare, Aurangabad (IN)

(73) Assignee: Lupin Limited, Mumbai (IN)

( * ) Notice: Subject to any disclaimer, the term of this patent is extended or adjusted under 35 U.S.C. 154(b) by 1585 days.

(21) Appl. No.: 10/495,961

(22) PCT Filed: Nov. 19, 2001

(86) PCT No.: PCT/IN01/00204
§ 371 (c)(1),
(2), (4) Date: May 18, 2004

(87) PCT Pub. No.: WO03/043607
PCT Pub. Date: May 30, 2003

(65) Prior Publication Data
US 2005/0031685 A1    Feb. 10, 2005

(51) Int. Cl.
*A61K 9/22* (2006.01)
(52) U.S. Cl. .......................... 424/468; 514/964
(58) Field of Classification Search .................. 424/468; 514/964
See application file for complete search history.

(56) References Cited

U.S. PATENT DOCUMENTS

| | | | |
|---|---|---|---|
| 5,419,917 A | 5/1995 | Chen et al. | |
| 5,948,440 A * | 9/1999 | Arora et al. | 424/468 |
| 6,267,986 B1 | 7/2001 | Jain et al. | |

FOREIGN PATENT DOCUMENTS

| | | |
|---|---|---|
| EP | 0 234 670 | 9/1987 |
| WO | WO 98/22091 | 5/1998 |
| WO | WO 00/15198 | 3/2000 |
| WO | PCT/IN00/00112 | 5/2002 |

OTHER PUBLICATIONS

National Cancer Institute Drug Dictionary, entry for probenecid, accessed Jan. 3, 2008.*
Chun, Kyung Hee et al, "Preparation of Sodium Alginate Microspheres Containing Hydrophilic b-lactam antibiotics," Arch. Pharm. Res. (1996). vol. 19 (No. 2), pp. 106-116.*
Hilton et al. "Use of Hydroxpropyl Methylcellulose Acetate Succinate in an Entric Polymer Matrix to Design Controlled-Release Tablets of Amoxicillin Trihydrate" *Journal of Pharmaceutical Sciences*. vol. 82, No. 7, Jul. 1993, pp. 737-743.
XP002172733 Database WPI, Section Ch, Week 197741, Derwent Publications Ltd., London GB; AN 1977-73627Y & JP 52 105220 A (Toyama Chem Co Ltd), Sep. 3, 1977 abstract.
Dhopeshwarkar et al., "Development of an oral sustained-release antibiotic matrix tablet using in-vitro/in-vivo correlations," *Drug Development and Industrial Pharmacy* (1994) 20 (11): 1851-1867
O'Grady et al., "Antibiotic and chemotherapy: Anti-infective agents and their use in therapy," *Churchill Livingstone Seventh Edition* (1997): 202-208.

* cited by examiner

*Primary Examiner* — Kamal Saeed
*Assistant Examiner* — Janet L Coppins
(74) *Attorney, Agent, or Firm* — Merchant & Gould P.C.

(57) ABSTRACT

An improved stable pharmaceutical composition for controlled release of an active ingredient comprises a betalactam antibiotic such as cephalexin, cefaclor or their pharmaceutically acceptable hydrates, salts or esters as active ingredient, a calcium salt and a mixture of hydrophilic polymers selected from the group consisting of at least one sodium alginate and one xanthan gum and with or without hydroxypropyl methylcellulose, said composition optionally containing probenecid. The composition may also contain one or more of a water soluble and/or water dispersible diluent, wherein the quantities of the hydrophilic polymers and water soluble and/or water dispersible diluents are such that the therapeutically effective active ingredient is released at a rate suitable for once or twice daily administration of the pharmaceutical composition.

27 Claims, 1 Drawing Sheet

Linear plot of mean serum concentration v/s time for improved controlled release cephalexin (2×750 mg) dose

PHARMACEUTICAL COMPOSITION FOR CONTROLLED RELEASE OF A BETA-LACTAM ANTIBIOTIC

FIELD OF THE INVENTION

This invention relates to an improved stabilized pharmaceutical composition of modified release tablets comprising a betalactam antibiotic or their pharmaceutically acceptable hydrates, salts or esters as the active ingredient, which would provide for controlled release of said actives and will also be capable of maintaining its dissolution characteristics upon storage, at ambient and accelerated conditions. The stabilized composition of the invention is also adapted to withstand the peristaltic pressure in the stomach and intestine, maintain the integrity of the composition and thereby avoid problems of dose dumping. Advantageously, the composition of the invention can be selectively provided to favour desired release of the therapeutically effective active ingredient such as at a rate suitable for once or twice daily administration of the pharmaceutical composition. The composition optionally contains probenecid as an antibiotic adjuvant.

BACKGROUND OF THE INVENTION

U.S. Pat. No. 6,267,986 B1 teaches preparation of a controlled release pseudoephdrine composition in combination with an antihistamine comprising two discrete zones. The first discrete zone comprises pseudoephdrine, one or more hydrophilic polymers, a salt of a polyuronic acid and a pharmaceutically acceptable salt of a group 11 metal ion and the second discrete zone comprises an antihistamine.

U.S. Pat. No. 5,419,917 discloses a controlled release hydrogel formulation for substantially zero-order release rate of drug from the hydrogel which is based on the use of an effective amount of a pharmaceutically acceptable ionizable compound. The hydrogel forming agent are being selected from the group consisting of hydroxypropyl methylcellulose, sodium alginate and xanthan and the ionizable compound being selected from the group consisting of alkali metal chlorides, organic acids, alkali metal sulfates and alkali metal alkyl sulfates, dihydrogen sodium phosphate and monohydrogen sodium phosphate.

A sustained release cephalexin tablet containing xanthan gum and sodium alginate as matrix formers was evaluated in human volunteers using in-vitrolin-vivo correlations. The optimized formulation containing 5% xanthan gum and 8% sodium alginate, decided on the basis of response surface analysis and computer simulation of cephalexin plasma levels versus time curves was used for clinical trials and was found to prolong the cephalexin blood levels up to 8 hours in humans. However, the relative bioavailability of cephalexin was reduced by about 30% and very little absorption was seen after six to eight hours, rendering the formulation not very useful for once daily regimen (see Dhopeshwarkar V., O'Keeffe J. C., Zatz J. L., Deeter R. and Horton M., *Drug Develp. Ind. Phar.*, 20, 1851, 1994).

Our PCT Application No. PCT/IN00/00112 relates to a pharmaceutical composition of modified release tablets comprising a betalactam antibiotic or their pharmaceutically acceptable hydrates, salts or esters as the active ingredient, and a mixture of hydrophilic polymers selected from the group consisting of at least one sodium alginate and at least one xanthan gum as controlled release matrix, and optionally probenecid. Inclusion of probenecid allows reduction in the amount of active incorporated in the polymeric matrix but can still provide desired once daily profile. The resulting modified release matrix formulation not containing probenecid may be administered in a once or twice daily regimen and the resulting modified release matrix formulation containing probenecid may be administered in a once daily regimen. However, it was observed that tablets become soft and irregular after about 6 hours of in-vitro dissolution studies, the integrity of the tablet and its shape is not maintained at a later stage after hydration. This soft irregular mass of the composition may not withstand the peristaltic pressure in the stomach and intestine, which could possibly lead to dose dumping in later stage.

Further, it was observed that the release of the active ingredient was faster from the samples stored for stability study under ambient and accelerated conditions, when compared to initial stage in-vitro dissolution data, which may render the composition ideally not suited for use as a controlled release composition having desired release profile.

OBJECTS OF THE INVENTION

The basic object of the present invention is to provide an improved stable composition of a betalactam antibiotic such as cephalexin, cefaclor or their pharmaceutically acceptable hydrates, salts or esters in a modified release matrix formulation, which would avoid the above discussed problems associated with stability of the composition and integrity of the composition and consequential dose dumping.

A further object of the present invention is to provide an improved stable composition of a betalactam antibiotic such as cephalexin, cefaclor or their pharmaceutically acceptable hydrates, salts or esters in a modified release matrix formulation, optionally containing probenecid such that the composition maintains its dissolution characteristics upon storage, at ambient and accelerated conditions.

Another object of the present invention is to provide an improved stable composition of a betalactam antibiotic such as cephalexin, cefaclor or their pharmaceutically acceptable hydrates, salts or esters in a modified release matrix formulation, optionally containing probenecid such that the integrity and shape of the composition is maintained even at the later stage of hydration.

SUMMARY OF THE INVENTION

Thus according to one aspect of the present invention there is provided a stable improved pharmaceutical composition for controlled release of an active ingredient comprising a controlled release matrix comprising i) a betalactam antibiotic or their pharmaceutically acceptable hydrates, salts or esters as the active ingredient in amounts of 30% to 90% by weight, ii) a mix of hydrophilic polymers in amount of 1% to 25% selected from the group consisting of at least one sodium alginate in amounts of 0.1% to 20%, and at least one xanthan gum in amounts of 0.1% to 20% and iii) a calcium salt in an amount of 8% to 20% by weight of sodium alginate.

In accordance with a preferred aspect the composition of the invention, in particular the hydrophilic polymers used therein incorporate along with the said sodium alginate and said xanthan gum optionally at least one hydroxypropyl methylcellulose, preferably in amount of 0.1% to 20% by weight of the controlled release matrix.

It is found that the above selective controlled release formulation of the invention avoids the shortcoming of integrity of the matrix composition comprising at least one sodium alginate and at least one xanthan gum and also takes care of the desired controlled release profile of the active. By inclusion of a hydroxypropyl methylcellulose in to the matrix, the integrity of the tablet is improved and its shape is maintained at a later stage after hydration so that it withstands the peristaltic pressure in the stomach and intestine thereby obviating the possibility of dose dumping.

Advantageously, the selective use of a calcium salt such as calcium sulphate in the defined range as disclosed above is also found to be advantageous in use with sodium alginate as a polymer matrix material for controlled release formulation. This is because calcium alginate when used as such in sustained release preparation forms a water insoluble gel, which has reduced diffusivity and erosion of gel layer. But addition of the selective calcium salt in dry state in the polymer matrix containing sodium alginate acts as a matrix stabilizing agent by in situ formation of a localized calcium alginate gel, as after ingestion of the composition, the solvent front passes up to the core of the composition resulting in formation of gel layer in a manner such that a gel layer contains combination of sodium and calcium alginate, which would erode faster in comparison to a gel layer containing only calcium alginate leading to desired release profile of the active from the composition.

Importantly, the above composition of the invention spends to the problems of stability of the tablets after storage at ambient and accelerated conditions, by selective incorporation of a calcium salt such as calcium sulphate in a defined range as matrix stabilising agent.

In accordance with a preferred aspect, the invention proposes the use of a hydroxypropyl methylcellulose into the matrix, which forms a strong gel structure. These hydrophilic polymers when used in appropriate concentrations, form the integrated matrix which provides the desired release profile, when the delivery system travels through the GIT, having varying physiological condition. Surprisingly, the polymers in appropriate combinations are not only effective compared to other commonly used polymers, but works at low concentrations. The combination of these polymers compliment each other such that, it overcomes the deficiencies associated with their use, when used alone.

The composition of the invention can optionally also contain one or more water soluble and/or water dispersible diluents, wherein the quantities of the hydrophilic polymers and water soluble and/or water dispersible diluents are such that the therapeutically effective active ingredient is released at a rate suitable for once or twice daily administration of the pharmaceutical composition. Inclusion of probenecid allows reduction in the amount of active incorporated in the hydrophilic polymer matrix but still provides the desired once a day profile.

The preferred betalactam antibiotic is selected from cephalexin, cefaclor or their pharmaceutically acceptable hydrates, salts or esters.

The modified release matrix formulation not containing probenecid prepared according to present invention may be administered once or twice daily. For Example, the effective therapeutic dose of the active that can be administered by compositions of present invention include 375 mg to 500 mg active twice daily or 750 mg to 1500 mg active once daily.

The modified release matrix formulation containing probenecid prepared according to present invention may be administered once daily. For example, the effective therapeutic dose of the active that can be administered by compositions of present invention include 500 mg to 1000 mg active and 500 mg to 1000 mg probenecid once daily.

It is to be understood that both the foregoing general description and the following detailed description are exemplary, but are not restrictive, of the invention.

DETAILED DESCRIPTION OF THE INVENTION

The composition of this invention is in the form of a matrix tablet comprising the active ingredient, hydrophilic polymers, a calcium salt, water soluble and/or water dispersible diluents, pharmaceutically acceptable tablet excipients, and antibiotic adjuvant if any, for controlling the release of active ingredients.

According to the present invention, the active ingredient is a betalactam antibiotic such as cephalexin, cefaclor or their pharmaceutically acceptable hydrates, salts or esters in a controlled release matrix. The cephalexin, cefaclor or their pharmaceutically acceptable hydrates, salts or esters may be present in an amount from about 30% to about 90% by weight of the controlled release matrix.

Further, the cephalexin, cefaclor or their pharmaceutically acceptable hydrates, salts or esters may be present in an amount from 100 mg to 2000 mg.

Examples of other cephalosporin antibiotics which may be used include cefuroxime, cefamandole, cefoxitin, cephalothin, moxalactam, cephapirin, ceffizoxime, cefonicid and, pharmaceutically acceptable hydrates, salts or esters thereof. Examples of other betalactam antibiotics, which may be used, are amoxicillin, ampicillin, and cloxacillin.

Examples of the calcium salts useful in the present invention are calcium sulphate, calcium citrate, disodium calcium edetate, calcium lactate, calcium ascorbate, calcium gluconate, calcium chloride. The preferred calcium salt is calcium sulphate.

Xanthan gum when used as a matrix forming agent in sustained release tablets, releases the drug slightly faster in acidic media, due to more rapid initial surface erosion than at higher pH. After hydration of the gum the drug release is essentially pH independent but the release of drug decrease exponentially.

Alginic acid is insoluble in aqueous media. However, as the pH is raised above 3, the alginic acid is partly converted to a soluble salt. Complete neutralization occurs around pH 4, where the alginic acid is completely converted to its corresponding salt. Sodium, potassium, magnesium and ammonium salts are examples of water-soluble alginate salts. Neutralization by calcium, barium and other multivalent alkali materials will produce insoluble alginate salts.

Thus when sodium alginate is used along with xanthan gum to form a controlled release matrix, it reduces the initial bursting effect and in later stages acts as a channeling agent to increase the release rate of the active.

It is known in the art that in gastric fluid the hydrated sodium alginate is converted into a porous, insoluble alginic acid skin. Once passed into the higher pH of the intestinal tract, the alginic acid skin is converted to a soluble viscous layer.

Alginate powders like sodium alginate when stored under cool, dry conditions in sealed container is stable and does not undergo microbial spoilage but due to slow reduction in degree of polymerization, its properties may be affected by storage. This is most easily observed as a reduction in viscosity of soluble alginates. This may be the reason for observed faster release of the active from the composition comprising of matrix prepared with a sodium alginate, a xanthan gum and a hydroxypropyl methylcellulose, on stability as compared to freshly prepared compositions.

Many drugs and drug metabolites are actively secreted by the proximal tubular active transport mechanism and interactions may arise from competition for these systems. Particularly with antibiotic therapy, active tubular secretion is a significant route of elimination. Drugs that use the same active transport system in the kidney tubules can compete with one another for secretion. Probenecid belongs to this class of drugs, which is able to compete successfully with some other drugs for an active secretion mechanism in the kidney tubule. This prevents them from being secreted into the tubular filtrate. Probenecid is later passively reabsorbed from the kidney tubules. Probenecid was extremely useful in the early days of penicillin when the combination raised and prolonged penicillin plasma levels Inhibition of the urinary excretion of penicillin and some cephalosporins has been used as a device to increase the biliary excretion of these agents, thereby raising the antibiotic concentrations in the biliary tract. This has been used to improve the efficacy of antibiotic treatment (Antibiotic and Chemotherapy: Anti-infective agents and their use in therapy, $7^{th}$ edition, Ed. by O'grady F., Finch R. G., Lambert H. P., Greenwood D.; Churchill Livingstone, 1997).

In the present invention probenecid is used as an antibiotic adjuvant for reducing the elimination rate and increasing the half-life of the therapeutically active ingredient. Inclusion of probenecid allows reduction in the amount of active incorporated in the hydrophilic polymer matrix but still provides the desired once a day profile.

For the purpose of the composition of the invention, sodium alginate used is preferably characterized by their viscosities in a 1% w/% aqueous solution as low viscosity (about 75 to about 150 cPs), medium viscosity (about 200 to about 400 cPs) and hitch viscosity (about 600 to about 1000 cPs); xanthan gum may be characterized as low viscosity (about 600 to about 1500 cs), medium viscosity (about 1550 to about 1850 cPs) and high viscosity (greater than about 1900 cPs); and hydroxypropyl methylcellulose may be characterized by their viscosity in a 2% w/w aqueous solution as low viscosity (less than 1000 cps), medium viscosity (about 1000 cps to about 10,000 cps) and high viscosity (greater then about 10,000 cps).

The different viscosity grade polymers may be used in the present invention, but in order to utilize minimum possible concentrations of the polymer to achieve the desired profiles, without compromising on the integrity of the matrix, medium or high viscosity grade polymers are preferred.

In a preferred embodiment of the present invention, the pharmaceutical composition comprises from about 30% to about 90% by weight of cephalexin, cefaclor or their pharmaceutically acceptable hydrates, salts or esters and about 1% to about 25% by weight of hydrophilic polymers comprising of sodium alginate in an amount from about 0.1% to about 20% by weight, xanthan gum in an amount from about 0.1% to about 20% by weight, and hydroxypropyl methylcellulose in an amount from about 0.1% to about 20% by weight of controlled release matrix, and calcium sulphate in an amount from about 8% to about 20% by weight of sodium alginate.

In a more preferred embodiment of the present invention, the pharmaceutical composition comprises from about 30% to about 90% by weight of cephalexin, cefaclor or their pharmaceutically acceptable hydrates, salts or esters and about 1% to about 20% by weight of hydrophilic polymers comprising of a medium or high viscosity grade sodium alginate in an amount from about 0.1% to about 15% by weight, a medium or high viscosity grade xanthan gum in an amount from about 0.1% to about 15% by weight, and a medium or high viscosity grade hydroxypropyl methylcellulose in an amount from about 0.1% to about 15% by weight of controlled release matrix, and calcium sulphate in an amount from about 8% to about 16% by weight of sodium alginate.

In one more preferred embodiment of the present invention, the pharmaceutical composition comprises from about 30% to about 90% by weight of cephalexin cefaclor or their pharmaceutically acceptable hydrates, salts or esters and about 1% to about 18% by weight of hydrophilic polymers comprising of a medium or high viscosity grade sodium alginate in an amount from about 1% to about 10% by weight, a medium or high viscosity grade xanthan gum in an amount from about 1% to about 10% by weight, and a medium or high viscosity grade hydroxypropyl methylcellulose in an amount from about 1% to about 10% by weight of controlled release matrix; and calcium sulphate in an amount from about 10% to about 14% by weight of sodium alginate.

Probenecid may be formulated as a controlled release or immediate release part, in an amount from about 250 mg to about 1000 mg.

The inclusion of probenecid in compositions of the present invention allows lowering of amount of active ingredient used. For example, therapeutically effective dose of the active ingredient that can be administered by the composition of the present invention containing probenecid include 500 to 1000 mg active with 500 to 1000 mg probenecid once daily, and therapeutically effective dose of the active that can be administered by the composition of the present invention not containing probenecid include 750 mg to 1500 mg of active once daily.

The composition may contain one or more of pharmaceutically acceptable excipients in an amount of about 1% to about 30% by weight of the total weight of the composition. These excipients may be water soluble or water dispersible. Examples of water soluble diluents that may be used in the present invention include lactose, mannitol, glucose, sorbitol, maltose, dextrates, dextrins and the like. Water dispersible diluent refers to insoluble pharmaceutical excipients, which disperse readily in water such as microcrystalline cellulose, starch, pre-gelatized starch, magnesium aluminum silicates and the like. In one preferred embodiment, the water soluble diluent is lactose in amounts from about 4% to about 20% by weight of the composition. In another preferred embodiment, the water dispersible diluent is microcrystalline cellulose present in amount from about 4% to about 20% by weight of the composition.

The composition may also contain tablet lubricants, at a concentration in the range of about 0.2% to 5% by weight of the composition. The lubricants that may be used include talc, stearic acid, magnesium stearate, colloidal silicon dioxide, calcium stearate, zinc stearate, hydrogenated vegetable oil and the like. Preferably the lubricant is magnesium stearate.

The immediate release probenecid part of the present invention contains a disintegrating agent at concentration in the range of about 2% to about 9% by weight of immediate release part. Preferably the disintegrating agent is sodium starch glycolate.

The pharmaceutical composition of the present invention may be prepared by procedures well known to formulation chemists. The method of manufacturing can affect the release characteristics of the composition. All the hydrophilic polymers are uniformly pre-blended with calcium sulphate, followed by the active ingredient, one or more water soluble or water dispersible diluents are either mixed together with lubricants and the blend is directly compressed into tablets or are granulated by compaction followed by sieving and the granules obtained are compressed into tablets. The active ingredient can be given as controlled release tablets for once or twice a day administration or as controlled release tablet along with separate probenecid tablets as a combipack to be administered simultaneously or coupled with probenecid into a single monolithic or bilayered tablets for once a day administration. The fines incorporated in the blend of active granules form about 12% to about 30% by weight of controlled release part, preferably from about 12% to about 20%.

For the purpose of this patent application, fines denote the particles having size less than 250 microns.

The above-mentioned process has the advantage over its granulation by aqueous or non-aqueous vehicle used conventionally. The active ingredient such as cephalexin or cefaclor, which are sensitive to moisture and heat, can be effectively processed without any difficulty. The polymers used in the composition of present invention, xanthan gum and sodium alginate also are unstable above 60° C. and 70° C. respectively. As the process is devoid of use of any solvents the potential problem of limiting the residual organic solvent is eliminated.

The controlled release matrix formulation of the present invention is not a mere admixture but has properties different from the sum total of the properties of its ingredients.

The probenecid part of the composition is prepared by mixing probenecid and one or more water soluble or water dispersible diluents together with lubricants and the blend is granulated by compaction followed by sieving and the granules obtained are lubricated and compressed into a tablet. The fines incorporated in the blend form about 10% to about 30% by weight of immediate release part, preferably from about 10% to about 20%.

The modified release matrix formulation not containing probenecid prepared according to present invention may be administered once or twice daily. For example, the effective therapeutic dose of the active that can be administered by compositions of present invention include 375 mg to 750 mg active twice daily or 750 mg to 1500 mg active once daily.

The modified release matrix formulation containing probenecid prepared according to present invention may be administered once daily. The effective therapeutic dose of the active that can be administered by compositions of present invention include 500 mg to 1000 mg, active and 500 mg to 1000 mg probenecid once daily.

The present invention is illustrated hereunder in greater detail in relation to non-limiting exemplary embodiments as per the following examples:

EXAMPLES

In the examples given below medium viscosity grade xanthan gum manufactured by Jungbunzlauer, Austria; sodium alginate (Keltone HVCR) manufactured by ISP Alginates; and hydroxypropyl methylcellulose of medium viscosity grade (Methocel K4M™), high viscosity grade (Methocel K15M™) manufactured by Dow Chemicals, USA has been employed. The dissolution results are given in respective tables for each example.

Effect of Calcium Sulphate (as a Matrix Stabilizing Agent) on In-Vitro Dissolution of Tablets on Storage at Accelerated Condition A) Tablet Containing Hydroxypropyl Methylcellulose

| Ingredients | Tablet with Calcium Sulphate | | Tablet without Calcium Sulphate | |
|---|---|---|---|---|
| | Weight (mg/tablet) | % w/w | Weight (mg/tablet) | % w/w |
| Cephalexin | 797.82 | 73.87 | 797.87 | 73.87 |
| Sodium Alginate | 43.20 | 4.00 | 86.40 | 8.00 |
| Xanthan Gum | 54.00 | 5.00 | 43.20 | 4.00 |
| Hydrxypropyl Methylcellulose (Methocel K15M) | 54.00 | 5.00 | 32.40 | 3.00 |
| Calcium Sulphate | 5.10 | 0.47 | — | — |
| Lactose Monohydrate | 109.63 | 10.15 | 103.93 | 9.62 |
| Magnesium Stearate | 16.20 | 1.50 | 16.20 | 1.50 |
| Total | 1080 | 100 | 1080 | 100 |

| Time (in hour) | % Cephalexin released (Tablet with calcium sulphate) | | | % Cephalexin released (Tablet without calcium sulphate) | | |
|---|---|---|---|---|---|---|
| | Initial | 1M[a] | 3M[b] | Initial | 1M[a] | 3M[b] |
| 1 | 22.5 | 22.6 | 21.6 | 22.0 | 22.4 | 22.9 |
| 2 | 35.7 | 34.3 | 33.5 | 37.1 | 36.8 | 37.3 |
| 3 | 45.0 | 42.3 | 41.3 | 44.5 | 44.7 | 45.0 |
| 4 | 44.4 | 43.7 | 43.5 | 45.6 | 50.4 | 52.1 |
| 6 | 48.5 | 48.5 | 49.1 | 48.6 | 68.0 | 73.6 |
| 8 | 58.1 | 58.2 | 58.9 | 56.8 | 89.0 | 94.1 |
| 10 | 69.4 | 69.9 | 69.8 | 67.2 | 99.9 | |
| 12 | 79.1 | 82.5 | 78.0 | 83.3 | | |
| 14 | 86.8 | 91.1 | 85.2 | 98.9 | | |

[a]Samples stored at accelerated conditions of 40° C., 75% relative humidity for 1 month.
[b]Samples stored at accelerated conditions of 40° C., 75% relative humidity for 3 months.

B) Tablet not Containing Hydroxypropyl Methylcellulose

| Ingredients | Tablet with Calcium Sulphate | | Tablet without Calcium Sulphate | |
|---|---|---|---|---|
| | Weight (mg/tablet) | % w/w | Weight (mg/tablet) | % w/w |
| Cephalexin | 797.87 | 73.87 | 800.86 | 74.14 |
| Sodium Alginate | 64.80 | 7.00 | 86.40 | 8.00 |
| Xanthan Gum | 75.60 | 6.00 | 75.60 | 7.00 |
| Calcium Sulphate | 9.07 | 0.84 | — | — |
| Lactose Monohydrate | 116.46 | 10.78 | 100.94 | 9.35 |
| Magnesium Stearate | 16.20 | 1.50 | 16.20 | 1.50 |
| Total | 1080 | 100 | 1080 | 100 |

| Time (in hour) | % Cephalexin released (Tablet with calcium sulphate) | | | % Cephalexin released (Tablet without calcium sulphate) | | |
|---|---|---|---|---|---|---|
| | Initial | 1M[a] | 3M[b] | Initial | 1M[a] | 3M[b] |
| 1 | 24.7 | 23.4 | 22.2 | 20.7 | 21.6 | 13.0 |
| 2 | 39.0 | 36.8 | 34.9 | 33.0 | 37.4 | 37.1 |
| 3 | 48.0 | 45.1 | 45.9 | 43.1 | 46.3 | 51.4 |
| 4 | 48.3 | 48.7 | 48.1 | 43.3 | 53.7 | 55.0 |
| 6 | 55.0 | 55.3 | 57.8 | 51.1 | 69.4 | 76.5 |
| 8 | 66.7 | 65.7 | 70.5 | 65.0 | 92.2 | 95.3 |
| 10 | 82.9 | 75.4 | 84.5 | 81.8 | | |
| 12 | 87.4 | 84.7 | 88.0 | 96.4 | | |
| 14 | 100.0 | 98.1 | 92.8 | 100.4 | | |

[a]Samples stored at accelerated conditions of 40° C., 75% relative humidity for 1 month.
[b]Samples stored at accelerated conditions of 40° C., 75% relative humidity for 3 months.

It would be evident from the above, that incorporation of a calcium salt such as calcium sulphate as a matrix stabilizing agent advantageously favours maintaining the stability of the composition as a control release formulation, and can maintain its dissolution characteristics after storage at accelerated conditions. Additionally, the use of a hydroxypropyl methylcellulose in addition to a xanthan gum and a sodium alginate, though provides composition, which maintains its physical integrity/shape in the later stages of hydration, it does not provide a composition, which can maintain its dissolution characteristics after storage of samples at accelerated conditions.

In accordance the further aspect of the invention the following illustrations demonstrate the selectivity in the use of calcium sulphate within the range of the 8%-20% by weight of sodium alginate in the controlled release formulation of the invention.

Concentration of Calcium Sulphate

C) Calcium Sulphate at Concentration of 5% by Weight of Sodium Alginate

| Ingredients | Weight (mg/tablet) | % w/w |
|---|---|---|
| Cephalexin | 797.87 | 73.87 |
| Sodium Alginate | 43.20 | 4.00 |
| Xanthan Gum | 54.00 | 5.00 |
| Hydroxypropyl Methylcellulose (Methocel K15M) | 54.00 | 5.00 |
| Calcium Sulphate | 2.16 | 0.20 |
| Lactose Monohydrate0 | 112.57 | 10.42 |
| Magnesium Stearate | 16.20 | 1.50 |
| Weight | 1080 | 100 |

| | % Cephalexin released | |
|---|---|---|
| Time (hour) | Initial | 1M[a] |
| 1 | 22.1 | 24.1 |
| 2 | 34.2 | 36.3 |
| 3 | 41.3 | 47.6 |
| 4 | 42.6 | 47.7 |
| 6 | 46.6 | 57.4 |
| 8 | 55.0 | 72.2 |
| 10 | 65.9 | 86.4 |
| 12 | 72.7 | 108.9 |
| 14 | 80.1 | |

[a]Samples stored at accelerated conditions of 40° C., 75% relative humidity for 1 month.

The above results demonstrate by way of an increase in the dissolution rate of sample stored at accelerated condition, that concentration of calcium salt has not been adequate for maintaining dissolution characteristics after storage at accelerated conditions.

D) Calcium Sulphate at Concentration of 12% by Weight of Sodium Alginate

| Ingredients | Weight (mg/unit) | % w/w |
|---|---|---|
| Cephalexin | 797.87 | 73.87 |
| Sodium Alginate | 43.20 | 4.00 |
| Xanthan Gum | 54.00 | 5.00 |
| Hydroxypropyl Methylcellulose (Methocel K15M) | 54.00 | 5.00 |
| Calcium Sulphate | 5.10 | 0.47 |
| Lactose Monohydrate | 109.63 | 10.15 |
| Magnesium Stearate | 16.20 | 1.50 |
| Weight | 1080 | 100 |

| | % Cephalexin released | |
|---|---|---|
| Time (hour) | Initial | 1M[a] |
| 1 | 22.5 | 22.6 |
| 2 | 35.7 | 34.3 |
| 3 | 45.0 | 42.3 |
| 4 | 44.4 | 43.7 |
| 6 | 48.5 | 48.5 |
| 8 | 58.1 | 58.2 |
| 10 | 69.4 | 69.9 |
| 12 | 79.1 | 82.5 |
| 14 | 86.8 | 91.1 |

[a]Samples stored at accelerated conditions of 40° C., 75% relative humidity for 1 month.

The dissolution characteristics of sample after storage at accelerated conditions can be maintained by incorporating appropriate concentration of a calcium salt by weight of sodium alginate.

E) Calcium Sulphate at Concentration of 25% by Weight of Sodium Alginate

| Ingredients | Weight (mg/tablet) | % w/w |
|---|---|---|
| Cephalexin | 797.87 | 73.87 |
| Sodium Alginate | 43.20 | 4.00 |
| Xanthan Gum | 54.00 | 5.00 |
| Hydroxypropyl Methylcellulose (Methocel K15M) | 54.00 | 5.00 |
| Calcium Sulphate | 10.80 | 1.00 |
| Lactose Monohydrate | 103.93 | 9.62 |
| Magnesium Stearate | 16.20 | 1.50 |
| Weight | 1080 | 100 |

| | % Cephalexin released |
|---|---|
| Time (hour) | Initial |
| 1 | 21.3 |
| 2 | 33.0 |
| 3 | 40.0 |
| 4 | 42.1 |
| 6 | 43.5 |
| 8 | 47.7 |
| 10 | 53.9 |
| 12 | 59.7 |
| 14 | 66.1 |

The above results reveal that the initial release is retarded when higher concentration of calcium salt is used which is again not acceptable.

The above illustrations clearly reveal that only when calcium salt is used in amounts within the range of 8%-20% by weight of sodium alginate, the desired release profile and stability of the compositions can be maintained which is lost when the amount of calcium salt used is beyond the above selected range.

Tablets without Probenecid

Cefaclor or cephalexin, a mixture of uniformly preblended hydrophilic polymers and calcium sulphate, lactose and/or microcrystalline cellulose were mixed uniformly and lubricated with magnesium stearate. The blend was compacted and the slugs obtained were milled to form granules. The sized granules were blended with the fines and the remaining lubricant and further compressed into tablets.

For Example 1 to Example 5, the tablets were tested for cefaclor release in 900 ml of 0.1 N hydrochloric acid for 1 hr, after which the dissolution medium was changed to pH 6.8 phosphate buffer 900 ml. The dissolution medium (pH 6.8 phosphate buffer) was replaced with fresh medium every hour thereafter. The tablets were placed into a 40 mesh basket (USP apparatus type-I) and were rotated at 100 rpm.

For the examples containing cefaclor the dissolution medium (pH 6.8 phosphate buffer) was replaced with fresh medium every hour thereafter. For the examples containing cephalexin only aliquots and not all of the pH 6.8 phosphate buffer were withdrawn and replaced with fresh medium at each interval.

Example 1

| Ingredients | Weight (mg/tablet) | % w/w |
|---|---|---|
| Cefaclor | 524.10 | 74.87 |
| Sodium Alginate | 24.50 | 3.50 |
| Xanthan Gum | 7.00 | 1.00 |
| Calcium Sulphate | 3.50 | 0.50 |
| Lactose Monohydrate | 126.90 | 18.12 |
| Magnesium Stearate | 14.00 | 2.00 |
| Total | 700 | 100 |

| Time (hour) | Percent Cefaclor Released (%) |
|---|---|
| 1 | 30.90 |
| 2 | 47.10 |
| 3 | 68.80 |
| 4 | 83.40 |

Example 2

| Ingredients | Weight (mg/tablet) | % w/w |
|---|---|---|
| Cefaclor | 524.10 | 74.87 |
| Sodium Alginate | 24.50 | 3.50 |
| Xanthan Gum | 7.00 | 1.00 |
| Calcium Sulphate | 3.50 | 0.5 |
| Microcrystalline Cellulose | 126.90 | 18.12 |
| Magnesium Stearate | 14.00 | 2.00 |
| Total | 700 | 100 |

| Time (hour) | Percent Cefaclor Released (%) |
|---|---|
| 1 | 30.30 |
| 2 | 48.80 |
| 3 | 73.10 |
| 4 | 87.90 |

Example 3

| Ingredients | Weight (mg/tablet) | % w/w |
|---|---|---|
| Cefaclor | 526.80 | 75.25 |
| Sodium Alginate | 24.50 | 3.50 |
| Xanthan Gum | 14.00 | 2.00 |
| Calcium sulphate | 3.50 | 0.50 |
| Lactose monohydrate | 117.20 | 16.74 |
| Magnesium Stearate | 14.00 | 2.00 |
| Total | 700 | 100 |

| Time (hour) | Percent Cefaclor Released (%) |
|---|---|
| 1 | 24.60 |
| 2 | 35.30 |
| 3 | 46.80 |
| 4 | 66.30 |
| 5 | 83.10 |
| 6 | 94.10 |

Example 4

| Ingredients | Weight (mg/tablet) | % w/w |
|---|---|---|
| Cefaclor | 526.80 | 75.26 |
| Sodium Alginate | 24.50 | 3.50 |
| Xanthan Gum | 3.50 | 0.50 |
| Hydroxypropyl Methylcellulose (Methocel K4M) | 10.50 | 1.50 |
| Calcium Sulphate | 4.90 | 0.70 |
| Lactose monohydrate | 115.80 | 16.54 |
| Magnesium Stearate | 14.00 | 2.00 |
| Total | 700 | 100 |

| Time (hour) | Percent Cefaclor Released (%) |
|---|---|
| 1 | 29.60 |
| 2 | 49.60 |
| 3 | 74.70 |
| 4 | 92.80 |

Example 5

| Ingredients | Weight (mg/tablet) | % w/w |
|---|---|---|
| Cefaclor | 789.40 | 75.18 |
| Sodium Alginate | 42.00 | 4.00 |
| Xanthan Gum | 15.75 | 1.50 |
| Hydroxypropyl Methylcellulose (Methocel K4M) | 21.00 | 2.00 |
| Calcium Sulphate | 5.88 | 0.56 |

-continued

| Ingredients | Weight (mg/tablet) | % w/w |
|---|---|---|
| Lactose monohydrate | 154.97 | 14.76 |
| Magnesium Stearate | 21.00 | 2.00 |
| Total | 1050 | 100 |

| Time (hour) | Percent Cefaclor Released (%) |
|---|---|
| 1 | 19.10 |
| 2 | 28.70 |
| 3 | 44.40 |
| 4 | 59.80 |
| 5 | 71.40 |
| 6 | 82.00 |

For example 6 to Example 11, the tablets were tested for cephalexin release in 900 ml of 0.1 N hydrochloric acid for 2 hr, after which the dissolution media was changed to pH 6.8 phosphate buffer 900 ml. The tablets were placed into a 40 mesh basket (USP apparatus type-I) and were rotated at 100 rpm.

Example 6

| Ingredients | Weight (mg/tablet) | % w/w |
|---|---|---|
| Cephalexin | 536.82 | 74.55 |
| Sodium Alginate | 43.20 | 6.00 |
| Xanthan Gum | 21.60 | 3.00 |
| Hydroxypropyl Methylcellulose (Methocel K4M) | 21.60 | 3.00 |
| Calcium Sulphate | 4.32 | 0.60 |
| Lactose monohydrate | 81.68 | 11.34 |
| Magnesium Stearate | 10.80 | 1.50 |
| Total | 720 | 100 |

| Time (hour) | Percent Cephalexin Released (%) |
|---|---|
| 1 | 28.60 |
| 2 | 43.90 |
| 3 | 55.80 |
| 4 | 74.10 |
| 5 | 98.20 |

Example 7

| Ingredients | Weight (mg/tablet) | % w/w |
|---|---|---|
| Cephalexin | 799.95 | 74.07 |
| Sodium Alginate | 64.80 | 6.00 |
| Xanthan Gum | 75.60 | 7.00 |
| Calcium Sulphate | 7.77 | 0.72 |
| Lactose monohydrate | 115.60 | 10.70 |
| Magnesium Stearate | 16.20 | 1.50 |
| Total | 1080 | 100 |

| Time (hour) | Percent Cephalexin Released (%) |
|---|---|
| 1 | 22.80 |
| 2 | 35.10 |
| 3 | 42.10 |
| 4 | 42.90 |
| 6 | 47.40 |
| 8 | 57.40 |
| 10 | 73.50 |
| 12 | 86.10 |
| 14 | 98.40 |

Example 8

| Ingredients | Weight (mg/tablet) | % w/w |
|---|---|---|
| Cephalexin | 800.94 | 74.16 |
| Sodium Alginate | 54.00 | 5.00 |
| Xanthan Gum | 75.60 | 7.00 |
| Calcium Sulphate | 7.56 | 0.70 |
| Lactose monohydrate | 125.70 | 11.64 |
| Magnesium Stearate | 16.20 | 1.50 |
| Total | 1080 | 100 |

| Time (hour) | Percent Cephalexin Released (%) |
|---|---|
| 1 | 21.70 |
| 2 | 35.20 |
| 3 | 45.10 |
| 4 | 45.30 |
| 6 | 50.60 |
| 8 | 62.50 |
| 10 | 78.50 |
| 12 | 81.70 |
| 14 | 93.20 |

Example 9

| Ingredients | Weight (mg/tablet) | % w/w |
|---|---|---|
| Cephalexin | 797.87 | 73.87 |
| Sodium Alginate | 64.80 | 6.00 |
| Xanthan Gum | 54.00 | 5.00 |
| Hydroxypropyl Methylcellulose (Methocel K15M) | 54.00 | 5.00 |
| Calcium Sulphate | 7.78 | 0.72 |
| Lactose monohydrate | 79.95 | 7.40 |
| Magnesium Stearate | 21.60 | 2.00 |
| Total | 1080 | 100 |

| Time (hour) | Percent Cephalexin Released (%) |
|---|---|
| 1 | 23.20 |
| 2 | 34.90 |

-continued

| Time (hour) | Percent Cephalexin Released (%) |
|---|---|
| 3 | 41.40 |
| 4 | 43.30 |
| 6 | 47.10 |
| 8 | 57.10 |
| 10 | 70.10 |
| 12 | 86.90 |
| 14 | 97.00 |

Example 10

| Ingredients | Weight (mg/tablet) | % w/w |
|---|---|---|
| Cephalexin | 797.87 | 73.87 |
| Sodium Alginate | 64.80 | 6.00 |
| Xanthan Gum | 32.40 | 3.00 |
| Hydroxypropyl Methylcellulose (Methocel K15M) | 32.40 | 3.00 |
| Calcium Sulphate | 7.77 | 0.72 |
| Lactose monohydrate | 128.54 | 11.90 |
| Magnesium Stearate | 16.20 | 1.50 |
| Total | 1080 | 100 |

| Time (hour) | Percent Cephalexin Released (%) |
|---|---|
| 1 | 23.90 |
| 2 | 37.10 |
| 3 | 46.30 |
| 4 | 47.20 |
| 6 | 58.70 |
| 8 | 77.60 |
| 10 | 92.10 |
| 12 | 98.20 |

Example 11

| Ingredients | Weight (mg/tablet) | % w/w |
|---|---|---|
| Cephalexin | 797.87 | 73.87 |
| Sodium Alginate | 43.20 | 4.00 |
| Xanthan Gum | 43.20 | 4.00 |
| Hydroxypropyl Methylcellulose (Methocel K15M) | 64.80 | 6.00 |
| Calcium Sulphate | 5.10 | 0.47 |
| Lactose monohydrate | 109.63 | 10.15 |
| Magnesium Stearate | 16.20 | 1.50 |
| Total | 1080 | 100 |

| Time (hour) | Percent Cephalexin Released (%) |
|---|---|
| 1 | 22.90 |
| 2 | 35.10 |
| 3 | 42.40 |

-continued

| Time (hour) | Percent Cephalexin Released (%) |
|---|---|
| 4 | 43.60 |
| 6 | 47.80 |
| 8 | 57.10 |
| 10 | 66.90 |
| 12 | 76.60 |
| 14 | 86.80 |

Tablets with Probenecid

Example 12

Cephalexin, a mixture of uniformly preblended hydrophilic polymers and calcium sulphate, lactose were mixed uniformly and lubricated with magnesium stearate. The blend was compacted and the slugs obtained were milled to form granules. The sized granules were blended with the fines and the remaining lubricant.

Probenecid, microcrystalline sodium, sodium starch glycolate, were screened through 30 mesh sieve. The blend was compacted and the slugs obtained were again milled to obtain granules. The sized granules were mixed with remaining sodium starch glycolate and magnesium stearate and fines, followed by compression of cephalexin granules on the precompressed probenecid granules.

The tablets were tested for cephalexin release in 900 ml of 0.1 N hydrochloric acid for 2 hrs after which the dissolution media was changed to pH 6.8 phosphate buffer 900 ml. The tablets weir placed into a 40 mesh basket (USP apparatus type I) and were rotated at 100 rpm. Further, fresh tablets were analysed for Probenecid release using 900 ml of pH 7.5 simulated intestinal fluid without pancreatin, USP apparatus type II at 50 rpm.

| Ingredients | Weight (mg) | % w/w |
|---|---|---|
| Controlled Release Part | | |
| Cephalexin | 536.82 | 74.55 |
| Sodium Alginate | 28.80 | 4.00 |
| Xanthan Gum | 21.60 | 3.00 |
| Hydroxypropyl Methylcellulose (Methocel K4M) | 28.80 | 4.00 |
| Calcium Sulphate | 4.03 | 0.37 |
| Lactose | 89.15 | 12.38 |
| Magnesium Sterate | 10.80 | 1.50 |
| Total | 720 | 100.00 |
| Immediate Release Part | | |
| Probenecid | 500.00 | 79.36 |
| Microcrystalline Cellulose | 95.50 | 15.16 |
| Sodium Starch Glycolate | 31.50 | 5.00 |
| Magnesium Sterate | 3.00 | 0.48 |
| Total | 630.00 | 100.00 |

| Time (hour) | Percent Cephalexin Released (%) |
|---|---|
| 1 | 25.14 |
| 2 | 37.76 |
| 3 | 44.80 |

| Time (hour) | Percent Cephalexin Released (%) |
|---|---|
| 4 | 47.49 |
| 6 | 63.61 |
| 8 | 78.05 |
| 10 | 96.40 |

| Time (min) | Percent Probenecid Released (%) |
|---|---|
| 10 | 98.80 |
| 20 | 102.20 |
| 30 | 103.30 |

Example 13

Cephalexin, uniformly preblended hydrophilic polymers and calcium sulphate, microcrystalline cellulose were mixed uniformly and lubricated with magnesium stearate. The blend was compacted and the slugs obtained were milled to form granules. The sized granules were blended with the fines and the remaining lubricant.

Probenecid, lactose, sodium starch glycolate were screened through 30 mesh sieve. The blend was compacted and slugs obtained were milled to obtain granules. The sized granules were mixed with remaining sodium starch glycolate, magnesium stearate and fines followed by compression of Cephalexin granules on pre-compressed Probenecid granules.

The tablets were tested for dissolution in 900 ml of 0.1 N hydrochloric acid for 2 hrs after which the dissolution media was changed to pH 6.8 phosphate buffer 900 ml, using 40 mesh basket (USP apparatus type I) and were rotated at 100 rpm. Further fresh samples were analysed for Probenecid release using 900 ml of pH 7.5 simulated intestinal fluid without pancreatin, USP apparatus type II at 50 rpm.

| Ingredients | Weight (mg/tablet) | % w/w |
|---|---|---|
| Controlled Release Part | | |
| Cephalexin | 536.82 | 74.55 |
| Sodium Alginate | 43.20 | 6.00 |
| Xanthan Gum | 36.00 | 5.00 |
| Calcium Sulphate | 6.01 | 0.84 |
| Microcrystalline cellulose | 87.13 | 12.10 |
| Magnesium Sterate | 10.80 | 1.50 |
| Total | 720 | 100 |
| Immediate Release Part | | |
| Probenecid | 500.00 | 79.36 |
| Lactose | 102.00 | 16.19 |
| Sodium Starch Glycolate | 25.00 | 3.97 |
| Magnesium Sterate | 3.00 | 0.48 |
| Total | 630.00 | 100.00 |

| Time (hour) | Percent Cephalexin Released (%) |
|---|---|
| 1 | 28.10 |
| 2 | 41.80 |
| 3 | 50.30 |
| 4 | 57.30 |
| 6 | 70.10 |
| 8 | 83.30 |
| 10 | 99.70 |

| Time (min) | Percent Probenecid Released (%) |
|---|---|
| 10 | 80.30 |
| 20 | 95.40 |
| 30 | 99.30 |

Example 14

Cephalexin, probenecid, a mixture of uniformly preblended hydrophilic polymers and calcium sulphate and microcrystalline cellulose were screened through 30 mesh screen and mixed with magnesium stearate. The blend was compacted and the slugs obtained were milled to obtain the granules. The sized granules were blended with fines and the remaining lubricant and further compressed into tablets.

The tablets were tested for cephalexin dissolution in 900 ml of 0.1N hydrochloric acid for 2 hrs after which the dissolution media was changed to pH 6.8 phosphate buffer 900 ml, using 40 mesh basket (USP apparatus type I) and were rotated at 100 rpm. Further fresh samples were analysed for probenecid release using 900 ml of pH 7.5 simulated intestinal fluid without pancreatin USP apparatus type II at 50 rpm.

| Ingredients | Weight (mg/tablet) | % w/w |
|---|---|---|
| Cephalexin | 536.82 | 38.34 |
| Probenecid | 500.00 | 35.71 |
| Sodium Alginate | 70.00 | 5.00 |
| Xanthan Gum | 56.00 | 4.00 |
| Hydroxypropyl Methylcellulose (Methocel K4M) | 70.00 | 5.00 |
| Calcium Sulphate | 7.00 | 0.50 |
| Microcrystalline cellulose | 142.68 | 10.19 |
| Magnesium Sterate | 17.50 | 1.25 |
| Total | 1400 | 100 |

| Time (hour) | Percent Cephalexin Released (%) | Percent Probenecid Released (%) |
|---|---|---|
| 1 | 23.60 | 42.90 |
| 2 | 42.70 | 69.70 |
| 3 | 54.60 | 85.50 |
| 4 | 61.20 | 100.90 |
| 6 | 70.10 | |
| 8 | 80.40 | |
| 10 | 96.90 | |

Example 15

Cefaclor, a mixture of uniformly preblended hydrophilic polymers and calcium sulphate, microcrystalline cellulose were mixed uniformly and lubricated with magnesium stearate. The blend was compacted and the slugs obtained were milled to form granules. The sized granules were blended with the fines and the remaining lubricant.

Probenecid, starch, sodium starch glycolate, were screened through 30 mesh sieve. The blend was compacted and the slugs obtained were milled to obtain granules. The sized granules were mixed with remaining sodium starch glycolate and magnesium stearate and fines, followed by compression of cefaclor granules on the pre-compressed Probenecid granules.

The tablets were tested for cefaclor release in 900 ml of 0.1 N hydrochloric acid for 2 hrs after which the dissolution media was changed to pH-6.8 phosphate buffer 900 nil. The tablets were placed into a 40 mesh basket (USP apparatus type-I) and were rotated at 100 rpm. The dissolution medium (pH 6.8 phosphate buffer) was replaced by fresh medium every hour. Further fresh tablet were analysed for Probenecid release using 900 ml of pH 7.5 simulated intestinal fluid without pancreatin, USP apparatus type II at 50 rpm.

| Ingredients | Weight (mg/tablet) | % w/w |
|---|---|---|
| Controlled Release Part | | |
| Cefaclor | 530.50 | 75.78 |
| Sodium Alginate | 28.00 | 4.00 |
| Xanthan Gum | 7.00 | 1.00 |
| Hydroxypropyl Methylcellulose (Methocel K4M) | 14.00 | 2.00 |
| Calcium Sulphate | 3.92 | 0.56 |
| Microcrystalline Cellulose | 106.08 | 15.15 |
| Magnesium Sterate | 10.50 | 1.50 |
| Total | 700 | 100 |
| Immediate Release Part | | |
| Probenecid | 500.00 | 79.36 |
| Starch | 70.61 | 11.21 |
| Sodium Starch Glycolate | 50.40 | 8.00 |
| Magnesium Sterate | 9.00 | 1.43 |
| Total | 630.00 | 100.00 |

| Time (hour) | Percent Cefaclor Released (%) |
|---|---|
| 1 | 24.60 |
| 2 | 45.20 |
| 3 | 50.60 |
| 4 | 61.30 |
| 6 | 75.90 |
| 8 | 89.20 |

| Time (min) | Percent Probenecid Released (%) |
|---|---|
| 10 | 96.80 |
| 20 | 99.10 |
| 30 | 100.80 |

Further the bioavailability study was conducted for long acting modified release matrix formulation without probenecid, one dose of 2 tablets×(750 mg cephalexin), prepared according to present invention. Eight healthy male volunteers were selected for the study in which each volunteer was administered a dose of the drug with 180 ml of water. The volunteers had a standard breakfast before taking the drug. The desired blood levels up to 18 to 20 hours were achieved with compositions without probenecid prepared according, to the invention, indicating that it can be used as once daily composition.

Figure 1:
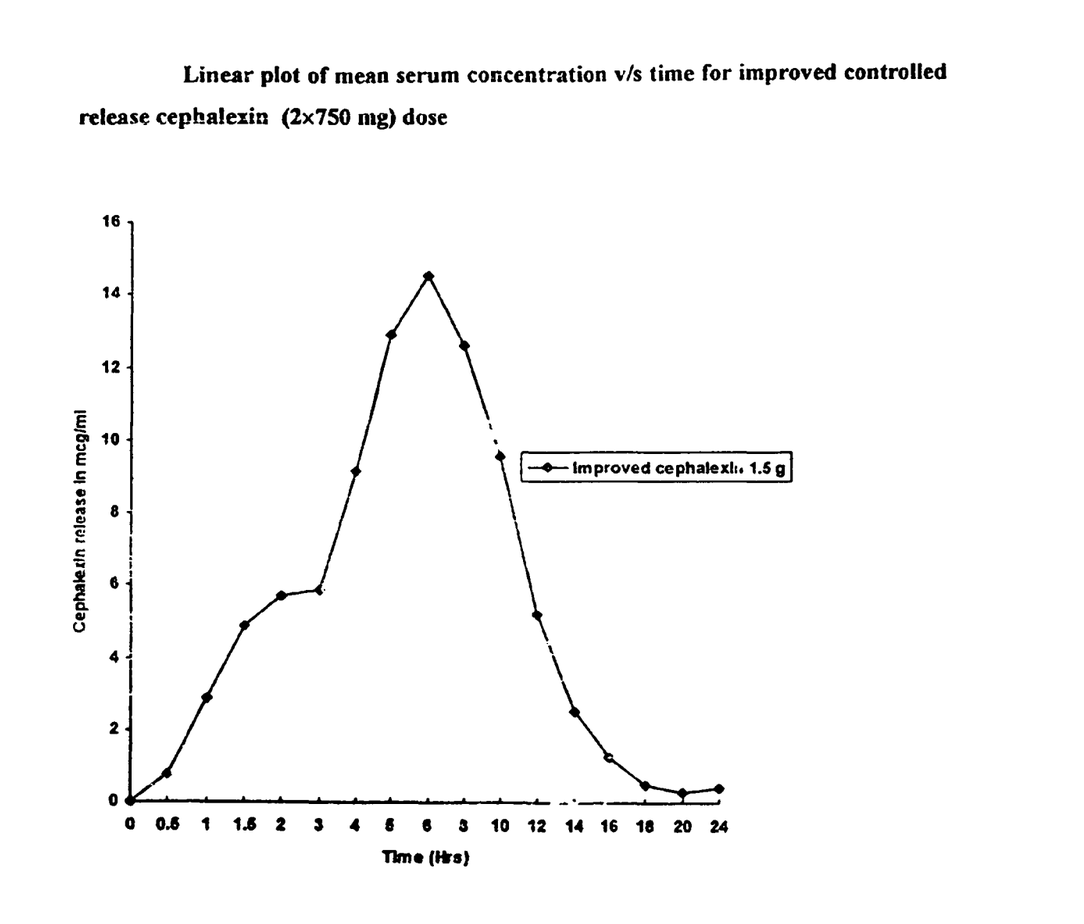

FIG. 1 shows a plot of blood level concentrations of modified release composition of the present invention, one dose of 2 tablets of cephalexin 750 mg. The plot clearly reveals the favourable bio-availability of the active achieved using the formulation of the invention.

The invention claimed is:

1. A pharmaceutical composition for controlled release of an active ingredient, comprising a controlled release matrix comprising:
   a) a β-lactam antibiotic or pharmaceutically acceptable salts thereof;
   b) one or more hydrophilic polymers comprising a sodium alginate, a xanthan gum, or a mixture thereof; and,
   c) one or more calcium salts comprising calcium sulphate, calcium citrate, disodium calcium edetate, calcium lactate, calcium ascorbate, calcium gluconate, calcium chloride, or a mixture thereof, wherein when the composition comprises sodium alginate, the calcium salt is present at about 8% to about 20% by weight of the sodium alginate.

2. The pharmaceutical composition of claim 1, wherein the one or more hydrophilic polymers further comprise a cellulose; and the amount of the one or more hydrophilic polymers is about 1% to about 25% by weight of the controlled release matrix.

3. The pharmaceutical composition of claim 1, wherein the composition is in a solid oral dosage form.

4. A controlled release pharmaceutical composition comprising a β-lactam antibiotic or pharmaceutically acceptable salts thereof, and a pharmaceutically acceptable carrier formed in situ from a mixture of one or more hydrophilic polymer(s) comprising a sodium alginate, a xanthan gum, or a mixture thereof; and one or more calcium salts comprising calcium sulphate, calcium citrate, disodium calcium edetate, calcium lactate, calcium ascorbate, calcium gluconate, calcium chloride, or a mixture thereof, wherein when the composition comprises sodium alginate, the calcium salt is present at about 8% to about 20% by weight of the sodium alginate.

5. The pharmaceutical composition of claim 4, wherein the composition releases about 0% to about 30% of active ingredient within 1 hour, about 25% to about 60% of active ingredient within 4 hours, about 45% to about 85% of active ingredient within 8 hours, and not less than about 60% of active ingredient in 12 hours, as measured according to in vitro dissolution testing.

6. The pharmaceutical composition of claim 5, wherein the dissolution testing is carried out using about 900 ml of 0.1N HCl for about 1 hour and a buffer having a pH of about 6.8 for the remaining period, using USP apparatus type I, rotating at 100 rpm.

7. The pharmaceutical composition of claim 1, further comprising a matrix stabilizing agent; and wherein the in vitro dissolution characteristics of the composition are essentially maintained upon storage for 1 month under accelerated stability conditions of 40° C. and 75% relative humidity.

8. The pharmaceutical composition of claim 5, wherein the tablet does not become soft and irregular even after about 6 hours of dissolution under in vitro conditions.

9. The pharmaceutical composition of claim 1, wherein the composition has improved stability and maintains its integrity and shape at a later stage of hydration within the gastrointestinal tract.

10. The pharmaceutical composition of claim 4, comprising:
- about 30% to about 90% by weight of the β-lactam antibiotic or pharmaceutically acceptable salts thereof;
- about 1% to about 20% by weight of the one or more hydrophilic polymers, selected from:
  - a) a medium or high viscosity grade sodium alginate in an amount from about 0.1% to about 15% by weight;
  - b) a medium or high viscosity grade xanthan gum in an amount from about 0.1% to about 15% by weight; or
  - c) a medium or high viscosity grade hydroxypropyl methylcellulose in an amount from about 0.1% to about 15% by weight of controlled release matrix; and
- wherein when the composition comprises the sodium alginate, the calcium salt is present at about 8% to about 16% by weight of the sodium alginate.

11. The pharmaceutical composition of claim 1, wherein the β-lactam antibiotic is selected from cephalexin, cefaclor or their pharmaceutically acceptable salts.

12. The pharmaceutical composition of claim 1 further comprising at least one water-soluble or water dispersible diluent present in an amount of from about 1% to about 30% by weight of the composition.

13. The pharmaceutical composition of claim 12, comprising about 4% to about 20% by weight water dispersible diluent selected from pharmaceutically acceptable sugars, starches, celluloses, or mixtures thereof.

14. The pharmaceutical composition of claim 1, further comprising about 0.2% to about 5% by weight of one or more pharmaceutically acceptable lubricants.

15. The pharmaceutical composition of claim 11, comprising about 250 mg to about 2000 mg cephalexin, cefaclor or their pharmaceutically acceptable salts.

16. A stable improved pharmaceutical composition for controlled release of β-lactam antibiotic or its pharmaceutically acceptable salts, the composition comprising a hydrophilic matrix and an adjuvant, the adjuvant comprising probenecid, wherein the hydrophilic matrix and the adjuvant are compressed together into a tablet dosage form or compressed separately into tablets and packed in a way to be administered simultaneously.

17. A process for the preparation of a pharmaceutical composition of β-lactam antibiotic, or its pharmaceutically acceptable salts having improved stability, the process comprising:

a) mixing the β-lactam antibiotic, or its pharmaceutically acceptable salts, with a composition comprising one or more hydrophilic polymers and one or more calcium salts;
- the one or more hydrophilic polymers comprising a sodium alginate, a xanthan gum, or a mixture thereof;
- the one or more calcium salts comprising calcium sulphate, calcium citrate, disodium calcium edetate, calcium lactate, calcium ascorbate, calcium gluconate, or calcium chloride;

b) further mixing such composition with one or more diluents, lubricants, or mixtures thereof to form a blend;

c) compacting and sizing the blend; and d) compressing the blend into tablets.

18. The process of claim 17 further comprising the step of mixing probenecid with one or more of the diluents, lubricants or mixtures thereof, or with a disintegrating agent prior to compressing the blend into tablets.

19. The pharmaceutical composition of claim 1, wherein the controlled release dosage form maintains plasma levels of β-lactam antibiotic above 2 μg/ml from about 8 to about 15 hours.

20. The pharmaceutical composition of claim 1, wherein the controlled release dosage form maintains plasma levels of β-lactam antibiotic above 4 μg/ml from about 7 to about 15 hours.

21. The pharmaceutical composition of claim 1, wherein the hydrophilic polymers comprise a mixture of xanthan gum, sodium alginate, and hydroxypropyl methylcellulose.

22. The pharmaceutical composition of claim 21, wherein the xanthan gum is present at about 0.1% to about 20% by weight of controlled release matrix.

23. The pharmaceutical composition of claim 21, wherein sodium alginate is present at about 0.1% to about 20% by weight of controlled release matrix.

24. The pharmaceutical composition of claim 21, wherein hydroxypropyl methylcellulose is present at about 0.1% to about 20% by weight of controlled release matrix.

25. The pharmaceutical composition of claim 13, comprising about 4% to about 20% water-soluble or water dispersible diluent selected from lactose, microcrystalline cellulose, or mixtures thereof.

26. The pharmaceutical composition of claim 14, comprising about 0.2% to about 5% by weight lubricant selected from magnesium stearate, talc, colloidal silicon dioxide, or mixtures thereof.

27. The pharmaceutical composition of claim 15, comprising about 100 mg to about 1000 mg cephalexin, cefaclor or their pharmaceutically acceptable salts.

* * * * *